United States Patent [19]

Gerhart et al.

[11] Patent Number: 4,719,313

[45] Date of Patent: Jan. 12, 1988

[54] GEM-DIHALO AND TETRAHALO-1,12-DIAMINO-4,9-DIAZA-DODECANES

[75] Inventors: Fritz Gerhart, Kehl Leutesheim, Fed. Rep. of Germany; Pierre Mamont, Strasbourg, France

[73] Assignee: Merrell Dow Pharmaceuticals Inc., Cincinnati, Ohio

[21] Appl. No.: 828,925

[22] Filed: Feb. 12, 1986

Related U.S. Application Data

[63] Continuation of Ser. No. 767,934, Aug. 21, 1985.

[51] Int. Cl.$^4$ ............................................. C07C 87/20
[52] U.S. Cl. .................... 564/512; 564/510; 514/672
[58] Field of Search ............ 564/510, 512, 487; 514/672

[56] References Cited

U.S. PATENT DOCUMENTS 4,004,996  1/1977  Kollonitsch ..................... 564/510

FOREIGN PATENT DOCUMENTS 7514240 12/1975 Netherlands.

OTHER PUBLICATIONS

*Chemical and Engineering News*, 29, (1951), p. 3042.

Primary Examiner—Charles F. Warren
Assistant Examiner—Elizabeth A. Hanley
Attorney, Agent, or Firm—Raymond A. McDonald

[57] ABSTRACT

Gem-dihalo and gem-tetrahalo-1,12-diamino-4,9-diazadodecane derivatives useful as antiproliferative or antitumor agents.

5 Claims, No Drawings

GEM-DIHALO AND TETRAHALO-1,12-DIAMINO-4,9-DIAZA-DODECANES

CROSS-REFERENCE TO RELATED APPLICATION

This is a continuation of application Ser. No. 767,934, filed Aug. 21, 1985.

BACKGROUND AND DESCRIPTION

It is a well known observation that the biosynthesis of natural polyamines, such as putrescine, spermidine and spermine, is elevated in rapidly proliferating cells relative to normal quiescent cells. Conversely, it is also known that the depletion of putrescine and spermidine leads to a reduction in cell proliferation.

Ornithine is the metabolic precursor of putrescine, which in turn, is the metabolic precursor of spermidine, which in turn, is the metabolic precursor of spermine. Metabolically, these biochemical conversions are catalysed by the enzymes ornithine decarboxylase, spermidine synthase and spermine synthase, respectively. Additionally, spermidine and spermine synthase enzymes utilize decarboxylated-S-adenosyl-L-methionine as a co-substrate, the reaction product of the S-adenosyl-L-methionine decarboxylase enzyme. Inhibitors of these enzymes, including inhibitors of S-adenosyl-L-methionine decarboxylase therefore, should serve to prevent the biosynthesis of putrescine and the higher polyamines derived therefrom, viz, spermidine and spermine, and should, theoretically, be effective as antiproliferative agents and/or antitumor agents.

However, in the past, the use of irreversible ornithine decarboxylase inhibitors or inhibitors of S-adenosyl-L-methionine decarboxylase, spermidine synthase and spermine synthase have not proven to be totally effective. Thus, for example, putrescine and spermidine are not essential for the maintenance of cell viability as long as the preexisting spermine pool is maintained above a certain critical level. Moreover, a total in vivo inhibition of the decarboxylase enzymes is difficult due to their rapid turnover.

Applicants have discovered a class of compounds which antagonize spermine functions in the cell. These compounds are highly effective inhibitors of cell growth in rapidly proliferating cells. Accordingly, the compounds of this invention are useful as antiproliferative and antitumor agents.

SUMMARY OF THE INVENTION

The present invention relates to certain selective gem-dihalo and tetrahalo derivatives of spermine. More particularly this invention relates to gem-dihalo or tetrahalo-1,12-diamino-4,9-diaza-dodecane derivatives having the formula

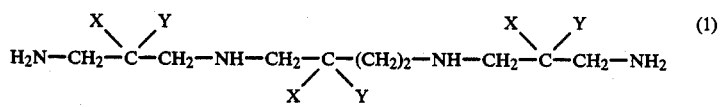

wherein X and Y represent hydrogen or halogen, with the proviso that in the case of the dihalo derivatives both halogens are present on one and only one carbon atom, and in the case of the tetrahalo derivatives the compounds are 2,2,11,11-halo-substituted; and the pharmaceutically acceptable salts thereof.

Additionally, certain aspects of this invention are directed to a process for the preparation of the compounds herein described, pharmaceutical compositions containing the same, and the use of these compounds as antitumor agents.

DETAILED DESCRIPTION OF THE INVENTION

As indicated in general formula (1) above the compounds of this invention form a specific class of gem-dihalo or gem-tetrahalo-spermines together with their pharmaceutically acceptable salts. As used throughout, however, a more definitive nomenclature will be employed, and the compounds will be designated as derivatives of gem-dihalo or gem-tetrahalo-1,12-diamino-4,9-diaza-dodecanes. When used herein, the term halo refers solely to chloro and fluoro derivatives.

All of the compounds encompassed within this invention are specific gem-dihalo derivatives or specific gem-tetrahalo derivatives. That is to say, the compounds of this invention are limited to either the 2,2-dihalo, the 6,6-dihalo or the 2,2,11,11-tetrahalo derivatives of 1,12-diamino-4,9-diaza-dodecane, as indicated by the proviso limitations. In view of the symmetrical nature of the molecule, the 2,2-dihalo derivatives are identical with the 11,11-dihalo derivatives, and such derivatives shall be designated throughout as 2,2-dihalo derivatives.

It will be noted that in the case the 2,2,11,11-tetrahalo derivatives due to their method of preparation, the substitutions at the 2 and 11 carbon atoms will be symmetrical. That is to say, the same substitution occuring at the 2-position must occur also at the 11-position.

The compounds of this invention encompassed within the scope of claim 1 include:
2,2-difluoro-1,12-diamino-4,9-diaza-dodecane,
2,2-dichloro-1,12-diamino-4,9-diaza-dodecane,
2-chloro-2-fluoro-1,12-diamino-4,9-diaza-dodecane,
6,6-difluoro-1,12-diamino-4,9-diaza-dodecane,
6,6-dichloro-1,12-diamino-4,9-diaza-dodecane,
6-chloro-6-fluoro-1,12-diamino-4,9-diaza-dodecane,
2,2,11,11-tetrafluoro-1,12-diamino-4,9-diaza-dodecane,
2,2,11,11-tetrachloro-1,12-diamino-4,9-diaza-dodecane, and
2,11-dichloro-2,11-difluoro-1,12-diamino-4,9-diaza-dodecane.

The pharmaceutically acceptable salts include those non-toxic organic or inorganic acid addition salts of the base compounds of Formula (1) above. Illustrative inorganic acids include hydrochloric, hydrobromic, sulfuric and phosphoric acids as well as metal salts such as sodium monohydrogen orthophosphate and potassium hydrogen sulfate. Illustrative organic acids which form suitable salts include the mono, di and tricarboxylic acids, such as acetic, glycolic, lactic, pyruvic, malonic, succinic, glutaric, fumaric, malic, tartaric, citric, ascorbic, maleic, hydroxymaleic, benzoic, p-hydroxybenzoic, phenylacetic, cinnamic, salicylic, 2-phenoxybenzoic and sulfonic acids such as methane sulfonic acid and 2-hydroxyethane sulfonic acid. Such salts can exist in either a hydrated or substantially anhydrous form.

All of the compounds of this invention are prepared in a logical sequence starting with the corresponding 2,2-dihalo-1,4-butanediols having the formula

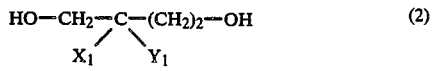  (2)

wherein $X_1$ and $Y_1$ represent chlorine or fluorine. These compounds are readily prepared by reacting the appropriate 2,2-dihalosuccinic acid with trifluoroacetic acid to form the corresponding 2,2-dihalosuccinic anhydrides. Cleavage of the anhydrides with methanol results in the formation of the corresponding methyl 2,2-dihalosuccinates. Reduction of the corresponding free acid function with borane-methyl sulfide complex results in the formation of the corresponding alcohols, i.e., the methyl 2,2-dihalo-4-hydroxybutanoates. Reduction of the ester function, for example using sodium borohydride, results in the formation of the desired starting materials, i.e., the 2,2-dihalo-1,4-butanediols (2).

The 6,6-dihalo-1,12-diamino-4,9-diaza-dodecane derivatives of this invention can be prepared in accordance with the following synthetic sequence wherein: $X_1$ and $Y_1$ = chlorine or fluorine

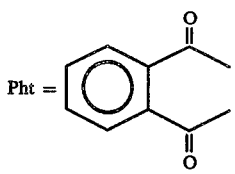

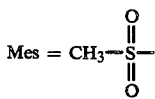

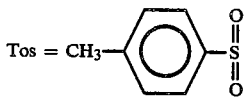

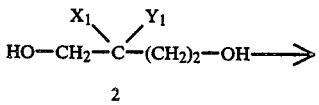

2

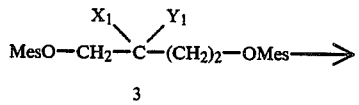

3

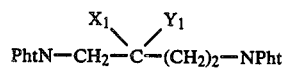

4

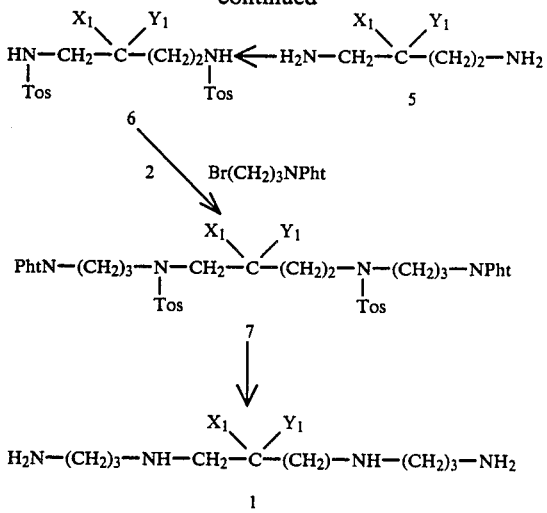

The compounds 2,2-dihalo-1,4-butanediol (2) are treated with two equivalents of methanesulfonyl chloride in the presence of pyridine to form the corresponding 1,4-bis-methanesulfonyloxy-2,2-dihalobutanes (3). Reaction of (3) with two equivalents of potassium phthalimide in a solvent such as dimethylformamide results in the formation of the corresponding 2,2-dihalo-1,4-diphthalimido-butanes (4). Heating of (4) with hydrazine in a solvent such as ethanol removes the phthaloyl protecting groups to form the key intermediates, 2,2-dihalo-1,4-diaminobutanes (5), which can be readily isolated as their dihydrohalide salts. The compound 2,2-difluoro-1,4-diaminobutane is a key intermediate useful in the preparation of 6,6-difluoro-1,12-diamino-4,9-diaza-dodecanes. Inasmuch as these 2,2-dihalo-1,4-diaminobutanes, represent such useful and novel compounds, they are specifically claimed herein as a part of the instant invention.

To avoid obtaining higher alkylated products, the primary amines of (5) are protected in a standard manner with p-toluenesulfonyl chloride to yield the corresponding 2,2-dihalo-1,4-di-p-toluenesulfonylaminobutanes (6). Alkylation of the protected amines (6) with two equivalents of 3-bromopropylphthalimide under anhydrous conditions in a suitable aprotic solvent, such as dimethylformamide in the presence of sodium iodide and potassium tert-butoxide, yields the corresponding 6,6-dihalo-1,12-diphthalimido-4,9-di-p-toluenesulfonyl-4,9-diaza-dodecanes (7).

These 4,9-diaza-dodecane derivatives (7) are deprotected in two steps, the first step involves heating with hydrazine in a solvent such as ethanol to remove the phthaloyl groups. The products so obtained are then heated with aqueous HBr to remove the protecting tosyl moieties. The final products obtained in this manner are the corresponding 6,6-dihalo-1,12-diamino-4,9-diaza-dodecanes (1), which can be readily isolated as their corresponding tetrahydrohalide salts, preferably as their tetrahydrobromide salts.

The 2,2-dihalo-1,12-diamino-4,9-diaza-dodecane derivatives of the present invention are prepared in accordance with the following reaction sequence, starting again with the appropriate 2,2-dihalo-1,4-butanediol (2). In this reaction sequence the symbols $X_1$, $Y_1$, Pht, Mes and Tos have the same meanings previously indicated.

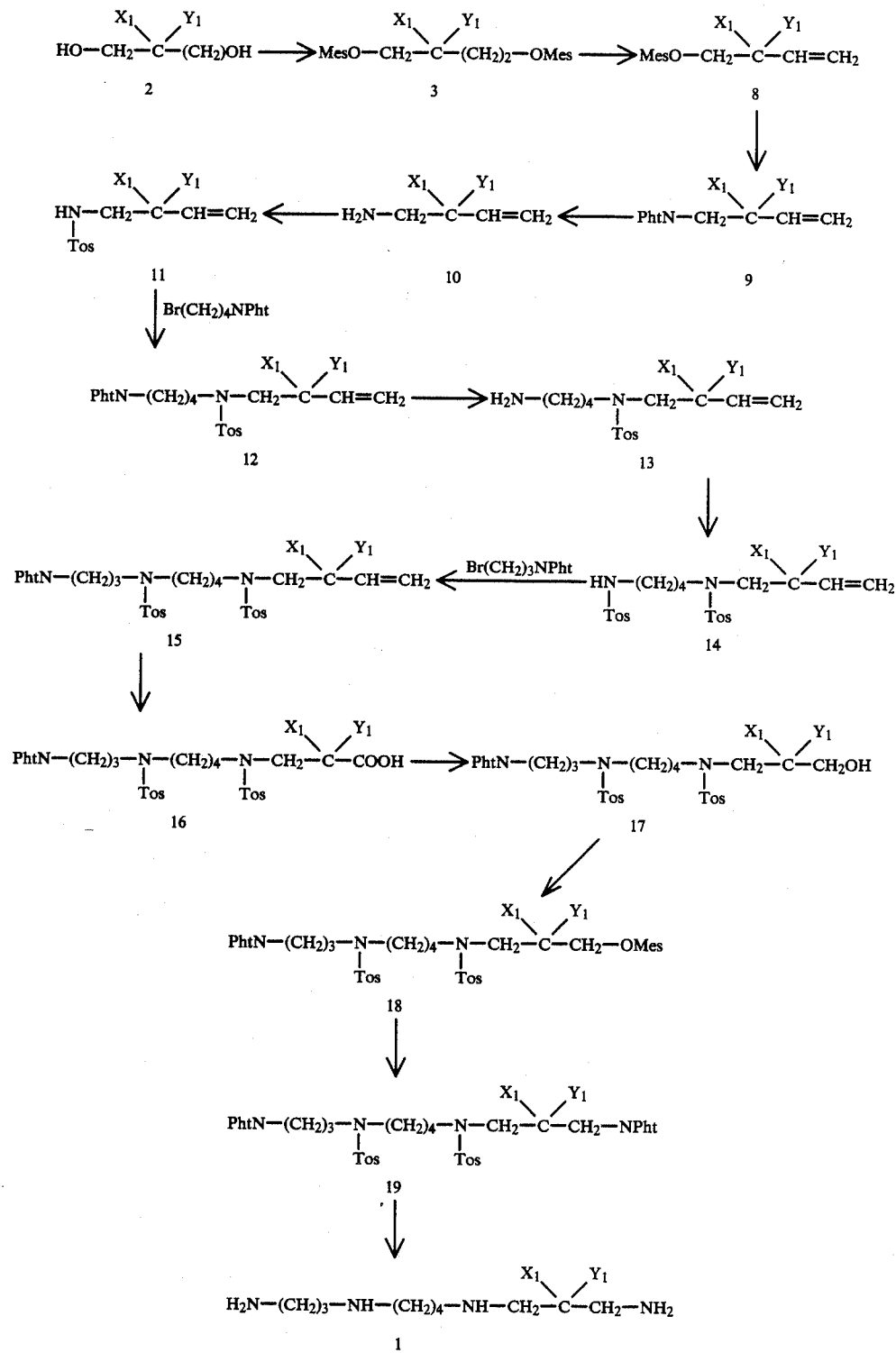

The 2,2-dihalo-1,4-butanediols (2) are treated with two equivalents of methanesulfonyl chloride in the presence of pyridine to form the corresponding 1,4-bis-methanesulfonyloxy-2,2-dihalobutanes (3). When (3) is heated with diazabicycloundecen in a solvent such as dimethylformamide, there is obtained the corresponding 1-methanesulfonyloxy-2,2-dihalo-3-butenes (8).

Reaction of (8) with potassium phthalimide in a solvent such as dimethylformamide results in the formation of the corresponding 1-phthalimido-2,2-dihalo-3-butenes (9). Cleavage of the phthaloyl derivative (9) with hydrazine in an alcoholic solvent provides the corresponding 1-amino-2,2-dihalo-3-butenes (10).

The primary amines (10) are protected by reaction with p-toluenesulfonyl chloride in a standard manner to obtain the corresponding N-(2,2-dihalo-3-butenyl)-p-toluenesulfonamides (11). Alkylation of the protected amine (11) with 4-bromobutylphthalimide in the presence of potassium tert.-butoxide under anhydrous conditions in a suitable solvent, such as dimethylformamide results in the formation of the corresponding N-(4-phthalimidobutyl)-N-(2,2-dihalo-3-butenyl)-p-toluenesulfonamides (12).

The action of hydrazine in a solvent such as ethanol upon (12) forms the corresponding 9-amino-3,3-dihalo-5-p-toluenesulfonyl-5-aza-1-nonenes (13), which upon treatment with p-toluenesulfonyl chloride yield the corresponding 9-p-toluenesulfonylamino-3,3-dihalo-5-p-toluenesulfonyl-5-aza-1-nonenes (14).

Alkylation of the protected amines (14) takes place with 3-bromopropylphthalimide in the presence of potassium tert-butoxide under anhydrous conditions in a solvent such as dimethylformamide to yield the corresponding 3,3-dihalo-13-phthalimido-5,10-di-p-toluenesulfonyl-5,10-diaza-1-tridecenes (15). Oxidation of the double bond (15) with KMnO₄ in an aqueous acetic acid solution results in the formation of the corresponding 2,2-dihalo-12-phthalimido-4,9-di-p-toluenesulfonyl-4,9-diaza-dodecanoic acids (16). Reduction of (16) with borane-methylsulfide complex forms the corresponding 2,2-dihalo-12-phthalimido-4,9-di-p-toluenesulfonyl-4,9-diaza-dodecanols (17).

Reaction of (17) with methanesulfonyl chloride in the presence of pyridine utilizing an anhydrous solvent such as dichloromethane results in the formation of the corresponding 2,2-dihalo-1-methanesulfonyloxy-12-phthalimido-4,9-di-p-toluenesulfonyl-4,9-diaza-dodecanes (18).

Further reaction of (18) with potassium phthalimide in anhydrous dimethylformamide results in the formation of the corresponding 2,2-dihalo-1,12-diphthalimido-4,9-di-p-toluenesulfonyl-4,9-diaza-dodecanes (19), which can be be deprotected in two stages, first by heating with hydrazine in a solvent such as ethanol to remove the phthaloyl groups, and then followed by heating the products so obtained with aqueous HBr in order to remove the protecting tosyl moieties. The desired products resulting therefrom are the corresponding 2,2-dihalo-1,12-diamino-4,9-diaza-dodecanes (1), which can be isolated as their corresponding tetrahydrohalide, and more particularly, as their tetrahydrobromide salts.

The 2,2,11,11-tetrahalo-1,12-diamino-4,9-diaza-dodecane derivatives of the present invention can be readily prepared in accordance with the following reaction sequence. In this sequence, the symbols $X_1$, $Y_1$, Pht, Mes and Tos have the same meanings as previously indicated with the proviso that both values for $X_1$ and both values for $Y_1$ must be the same.

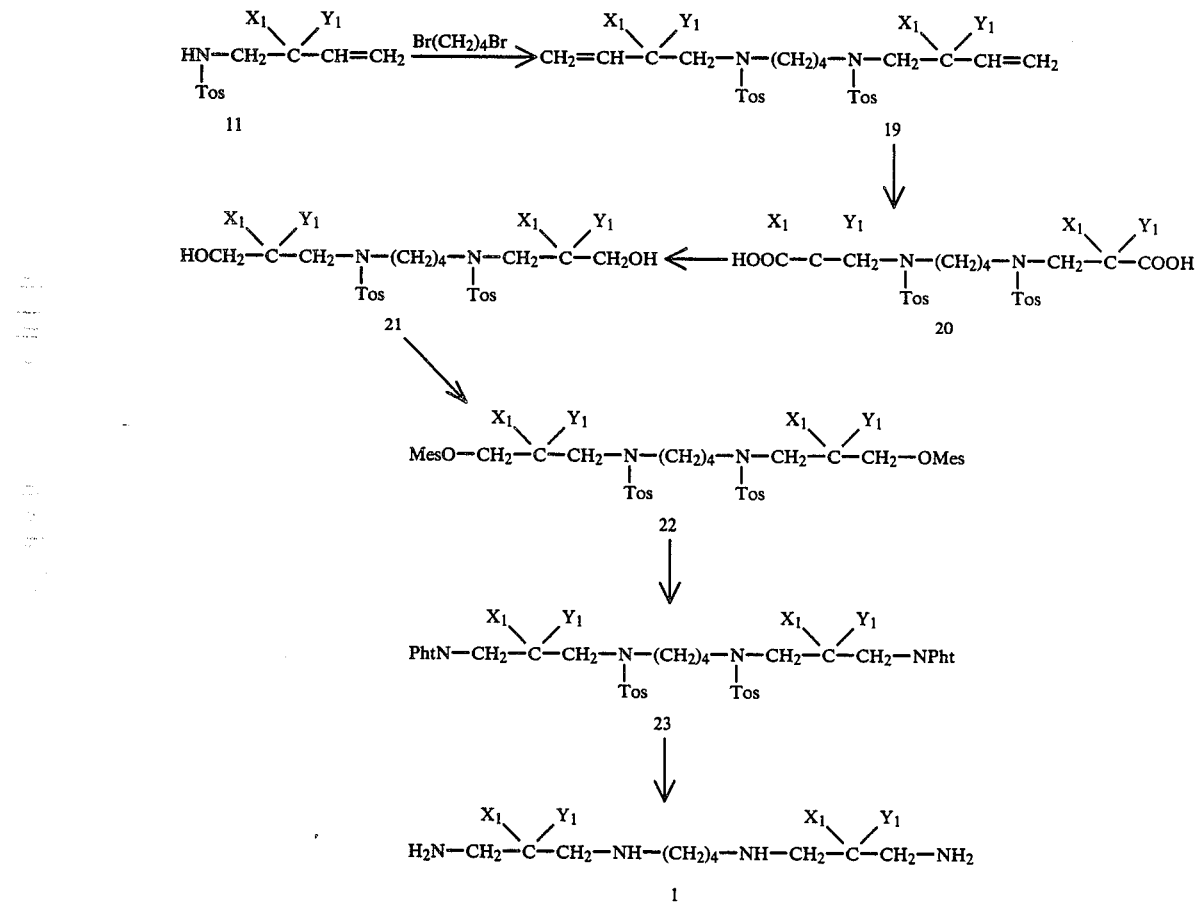

Two equivalents of the compounds, N-(2,2-dihalo-3-butenyl)-p-toluenesulfonylamide (11), prepared as indicated in accordance with the previous reaction sequence, can be symmetrically dialkylated with one equivalent of 1,4-dibromobutane under anhydrous conditions in the presence of potassium tert.-butoxide, utilizing a solvent such as dimethylformamide, to form the corresponding 3,3,12,12-tetrahalo-5,10-di-p-toluenesulfonyl-5,10-diaza-1,13-tetradecadienes (19).

Oxidation of the double bonds of (19), utilizing KMnO₄ in an aqueous acetic acid solution results in the formation of the corresponding 2,2,11,11-tetrahalo-4,9-di-p-toluenesulfonyl-4,9-diaza-1,12-dodecanedioic acids (20). Reduction of (20) with borane-methylsulfide complex forms the corresponding 2,2,11,11-tetrahalo-4,9-di-p-toluenesulfonyl-4,9-diaza-1,12-dodecanediols (21).

Reaction of (21) with methanesulfonyl chloride in the presence of pyridine, utilizing an anhydrous solvent such as dichloromethane, results in the preparation of the corresponding 1,12-methanesulfonyloxy-2,2,11,11-tetrahalo-4,9-di-p-toluenesulfonyloxy-4,9-diaza-dodecanes (22). Further reaction of (22) with potassium phthalimide in anhydrous dimethylformamide yields the corresponding 1,12-diphthalimido-2,2,11,11-tetrahalo-4,9-di-p-toluenesulfonyl-4,9-diaza-dodecanes (23).

The compounds (23) can be deprotected in two stages, first by heating with hydrazine in a solvent such as ethanol to remove the phthaloyl groups, and secondly by heating the products so obtained with aqueous HBr so as to remove the protecting tosyl moieties. The products so obtained are the corresponding desired 2,2,11,11-tetrahalo-1,12-diamino-4,9-diaza-dodecanes (1), which can be readily isolated as their tetrahydrobromide salts (1).

The compounds of the present invention are useful as antiproliferative and antitumor agents. The mechanism by which these compounds function is not known. What is known, however, is that when the compounds of this invention are added to a culture medium of growing rat hepatoma tissue culture (HTC) cells, a marked reduction of cell growth occurs. In combination with known ornithine decarboxylase inhibitors, such as 2-difluoromethyl-2,5-diaminopentanoic acid (DFMO) or [2R,5R]-6-heptyne-2,5-diamine (R,R-MAP), a further inhibition of cell growth occurs.

The compounds of this invention have also been found to be capable of slowing neoplastic cell proliferation when tested in standard animal tumor models. A preferred manner of utilizing these compounds is in combination with DFMO or [R,R]-MAP, or in combination with other therapeutic methods or agents known to affect polyamine metabolism in the treatment of neoplasms in animals. As used herein, the term animals is taken to mean warm blooded mammals, such as mice, rats, dogs, cats, guinea pigs, cows, horses and humans.

The compounds of this invention can be utilized both prophylactically and therapeutically. The amount of active ingredient for therapeutic administration can vary over a wide range and is dependent upon such factors as the species of animal to be treated, its age, health, sex, weight, nature and the severity of the condition being treated. Generally, a therapeutically effective amount of the active ingredient to be administered will range from about 0.2 to 5 grams, and preferably from 0.5 to 3 grams per day. For prophylactic administration, corresponding lower doses of from 0.05 to 2 grams per day can be utilized.

When administered in combination with other ornithine decarboxylase inhibitors, such as DFMO or [R,R]-MAP, an amount of from 0.1 to 4 grams of the particular gem-dihalo or tetrahalo-1,12-diamino-4,9-diaza-dodecane and from 0.5 to 10 grams of the ornithine decarboxylase inhibitor are administered per day.

The compounds of this invention can be orally administered. Illustrative dosage levels for oral administration range from 2 to 50 mg kg of body weight. Preferably, from 10 to 20 mg per kg of the gem-dihalo or tetrahalo-1,12-diamino-4,9-diaza-dodecane are orally administered per day in divided doses. In those instances where the drug is administered via the parenteral route, corresponding lower doses are employed. When administered in combination with ornithine decarboxylase inhibitors, the compounds can be administered in standard dosage unit forms, such as tablets, capsules, dragees, lozenges, elixirs, emulsions, suspensions and various intravenous, intramuscular or intradermal suspensions.

When administered orally, the preferred dosage form is that of a tablet or capsule. The amount of active ingredient contained in each dosage unit will, of course, vary depending upon the particular species of the gem-dihalo or tetrahalo-1,12-diamino-4,9-diaza-dodecane employed, and the particular dosage form utilized. Generally, a given dosage unit will contain from 10 to 500 mg of the active ingredient in addition to the various pharmaceutical excipients contained therein. Tablets containing from 100 to 400 mg of the active ingredient, are the preferred dosage unit and can be administered b.i.d., or t.i.d. or q.i.d.

In preparing solid dose forms such as tablets, the active ingredient is generally blended with conventional pharmaceutical carriers or excipients such as gelatin, various starches, lactose, calcium phosphate or powdered sugar. The term pharmaceutical carrier as used herein also includes lubricants employed to improve the flow of tablet granulations and which prevent adhesion of tablet material to the surfaces of tablet dies and punches. Suitable lubricants include, for example, talc, stearic acid, calcium stearate, magnesium stearate and zinc stearate. Also included within the definition of a pharmaceutical carrier as used herein, are disintegrating agents added to assist the breakup and dissolution of tablets following administration, as well as coloring and/or flavoring agents to enhance the aesthetic qualities of the tablets and make them more acceptable to the patient.

Suitable liquid excipients for the preparation of liquid dosage unit forms include water and alcohols such as ethanol, benzyl alcohol and the polyethylene glycols, either with or without the addition of a surfactant. In general, the preferred liquid excipients, particularly for injectable preparations, include water, saline solution, dextrose and glycol solutions such as an aqueous propylene glycol or an aqueous solution of polyethylene glycol.

Liquid preparations to be used as sterile injectable solutions will ordinarily contain from about 0.5 to about 25% by weight, and preferably from about 1 to about 10% by weight, of the active ingredient in solution. In certain topical and parenteral preparations, various oils can be utilized as carriers or excipients. Illustrative of such oils are mineral oils, glyceride oils such as lard oil, cod liver oil, peanut oil, sesame oil, corn oil and soybean oil. For insoluble compounds, suspending agents may be added as well as agents to control the viscosity, as for example, magnesium aluminum silicate or carboxymethylcellulose. In addition to these excipients, buffers, preservatives and emulsifying agents may also be added.

The proportion of the active ingredient employed in parenteral dosage unit forms ranges from 0.05 to about 20% by weight, preferably from about 0.1 to about 10% by weight of the total liquid composition, the remaining component or components comprising any of the various pharmaceutical excipients previously mentioned. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above-identified HLB, or a mixture of two or more components having the desired HLB. Illustrative of surfactants useful in parenteral formulations are the class of polyoxyethylene sorbitan fatty acid esters as, for example, sorbitan monooleate and the high molecular weight adducts of ethylene oxide with a hydrophobic base, formed by the condensation of propylene oxide with propylene glycol.

The invention described herein is more particularly illustrated in conjunction with the following specific preparations, but is not necessarily limited thereto.

PREPARATION OF 6,6-DIFLUORO-1,12-DIAMINO-4,9-DIAZA-DODECANE

2,2-Difluoro-1,4-butanediol 2,2-Difluorosuccinic acid (120 g, 0.78 moles) and trifluoroacetic anhydride (540 mL) are refluxed (bath temperature 80° C.) for 2 hours. Most of the trifluoroacetic acid is distilled utilizing a short Vigreux column, the final traces are removed under vacuum (12 mm Hg, 50° C.) and finally by stripping twice with carbontetrachloride. The oily residue solidifies on scratching with petroleum ether. Filtration and washing with petroleum ether yields 2,2-difluorosuccinic anhydride as slightly violet crystals: 98 g (92%).

The 2,2-difluorosuccinic anhydride (98 g, 0.72 moles) is dissolved in dichloromethane and slowly added with stirring to methanol, cooled in an ice bath. The mixture is kept at room temperature overnight, evaporated and stripped twice with carbon tetrachloride to yield methyl 2,2-difluorosuccinate as a slightly brownish oil: 121 g (100%).

In a 4 L flask equipped with a reflux condenser and 1 L dropping funnel, a solution of $BH_3.Me_2S$ complex (10M, 88 mL) in dry dichloromethane (1 L) is slowly added over a 2 hour period to a stirred solution of the methyl 2,2-difluorosuccinate (120 g, 0.714 moles) in dry tetrahydrofuran at 20° C. After refluxing (bath temperature 80° C.) for about 15 hours, the mixture is allowed to cool to room temperature and methanol (1 L) is slowly added. Evaporation yields methyl 2,2-difluoro-4-hydroxybutyrate as an oil which is stripped with methanol (1 L) and finally with $CCL_4$ to yield a yellow oil: 100 g (92%).

To a cold (0° C.) solution of sodium borohydride (10.3 g, 0.272 moles) in ethanol, a solution of the methyl 2,2-difluoro-4-hydroxybutyrate (55 g, 0.36 moles) in ethanol is slowly added, while maintaining the internal temperature of the reaction mixture between −50° C. and 0° C. The mixture is stirred for 1 hour at 0° C., then, an approximately 4N solution of HCl gas in methanol (200 mL) is carefully added. Sodium chloride is filtered, the methanol is removed under vacuum, and the residue is dissolved in ethanol. Additional NaCl is again removed by filtration (membrane filter) and evaporation of the filtrate yields the compound 2,2-difluoro-1,4-buanediol as a colorless oil when distilled in a Kugelrohr at 150° C./0.05 mm Hg; 41 g (90%).

2,2-Difluoro-1,4-diaminobutane

To a stirred mixture of 2,2-difluoro-1,4-butanediol (12.97 g, 103 mM), dry pyridine (65 mL) and dichloromethane (200 mL), is slowly added a solution of methanesulfonyl chloride (23.6 g) in dichloromethane (50 mL). Stirring is continued overnight, and the mixture is washed with 2N HCl (twice), 10% aqueous $NaHCO_3$ until neutral, and finally with water. The organic solution is dried ($MgSO_4$) and evaporated to yield 1,4-bis-methanesulfonyloxy-2,2-difluorobutane as a slightly yellow oil (25.4 g, 87.5%) which crystallizes on scratching with dry ether: white crystals, 22.3 g (77%).

The compound 1,4-bis-methanesulfonyloxy-2,2-difluorobutane (66 g, 234 mM), potassium phthalimide (97 g, 10% excess) and dry DMF (700 mL) are stirred and heated (bath temperature 110° C.) under nitrogen for 110 hours. Most of the DMF is removed under vacuum (oil pump) and water is added to the residue. The precipitated material is filtered, washed three times with water, dissolved in chloroform, and washed with 1N NaOH (twice) and brine (twice). After drying the organic solution ($Na_2SO_4$) and concentrating, the compound 2,2-difluoro-1,4-diphthalimido-butane begins to crystallize. Hexane is added, the solid material which results is collected and washed with ether to yield white crystals: 69.55 g (77%).

Under nitrogen and with efficient stirring a mixture of 2,2-difluoro-1,4-diphthalimido-butane: (69.55 g (180.6 mM), tetrahydrofuran (361 mL) and 361 mL of a 1N solution of hydrazine hydrate in ethanol are heated overnight at 90° C. (bath temperature). After addition of 6N HCl (700 mL), stirring and heating are continued for 1½ hours. The reaction mixture is cooled (ice bath), and the precipitate is filtered (ethanol wash). The filtrate is evaporated, the residue is taken up in water, filtered, and evaporated again. This procedure is repeated once again using a membrane filter (Millipore). The residue is stripped with isopropanol (twice) and ethanol (twice) to remove the final traces of water. Digestion with ethanol and subsequent filtration of the product so obtained, results in the formation of white crystals that are successively washed with ethanol, acetone and ether: 30.9 g (87%). This material is recrystallized by dissolving in the minimum amount of hot water (approximately 50 mL), filtering and adding ethanol to form pure 2,2-difluoro-1,4-diaminobutane as the dihydrochloride salt: 22 g (61.8%).

Calc'd for $C_4H_{12}Cl_2F_2N_2$: C, 24.38; H, 6.14; N, 14.22. Found: C, 24.33; H, 5.19; N, 14.24.

6,6-Difluoro-1,12-diphthalimido-4,9-di-p-toluenesulfonyl-4,9-diaza-dodecane

To a mixture of 2,2-difluoro-1,4-diaminobutane dihydrochloride (1.57 g, 8 mM), triethylamine (3.23 g, 4 equivalents) and dry dichloromethane is slowly added with stirring a solution of toluenesulfonyl chloride (3.04 g, 2 equivalents) in dichloromethane. After stirring overnight at room temperature, additional dichloromethane is added. The reaction mixture is washed with 1N HCl (twice), brine (twice), dried ($Na_2SO_4$) and evaporated to yield white crystals: 3 g. The resulting material is digested with ether and thoroughly washed with ether to yield pure 2,2-difluoro-1,4-di-p-toluenesulfonylamino-butane: 2.45 g (71%).

Under nitrogen, potassium tert-butoxide (1.3 g, 2 equivalents) is added to a stirred solution of 2,2-difluoro-1,4-di-p-toluenesulfonylamino-butane (2.45 g, 5.67 mM) in dry dimethylformamide (5 mL). After 30 minutes at room temperature, additional dimethylformamide (5 mL), N-3-bromopropylphthalimide (3.04 g, 2 equivalents), and sodium iodide (170 mg) are added. The mixture is stirred overnight, the dimethylformamide is removed under vacuum (oil pump). Water (250 mL) is added to the residue, and the precipitate is filtered, washed with water and dried over $P_2O_5$: 4.57 g. The crude material is recrystallized from chloroform/ether to yield pure 6,6-difluoro-1,12-diphthalimido-4,9-di-p-toluenesulfonyl-4,9-diaza-dodecane as white crystals: 3.45 g (75%).

6,6-Difluoro-1,12-diamino-4,9-diaza-dodecane

A mixture of 6,6-difluoro-1,12-diphthalimido-4,9-di-p-toluenesulfonyl-4,9-diaza-dodecane (3.4 g, 4.22 mM), ethanol (8.5 mL) and 8.5 mL of a 1N solution of hydrazine hydrate in ethanol is stirred and heated (bath temperature: 90° C.) overnight. Evaporation and stripping twice with methanol yields a residue which is dissolved in a mixture of water (20 mL), methanol (20 mL), and concentrated HCl (40 mL), and heated (bath temperature: 90° C.) under reflux for 3 hours. The reaction mixture is cooled, filtered and evaporated, and the residue is dissolved in hot 1N HCl. The solution is filtered, the filtrate is evaporated, and the residue is stripped with isopropanol (twice) and ethanol (twice). The residue is dissolved in ethanol, ether is added, and upon evaporation of the solvent, there is obtained 1,12-diamino-6,6-difluoro-4,9-di-p-toluenesulfonyl-4,9-diazadodecane as a white crystalline foam: 2.7 g (quantitative yield).

The compound 1,12-diamino-6,6-difluoro-4,9-di-p-toluenesulfonyl-4,9-diaza-dodecane (2.7 g, 4.36 mM) and 47% aqueous HBr are refluxed (bath temperature: 110° C.) for 17 hours. After cooling to room temperature, the solution is carefully extracted with ether (three times) and finally with chloroform. Evaporation of the aqueous phase, followed by stripping with isopropanol (twice) and ethanol (twice) produces a solid residue which is digested with acetone, collected, and washed with acetone (three times), ethanol (three times) and finally with ether: white crystals, 1.8 g (74%). This material is recrystallized by dissolving in hot (80° C.) aqueous ethanol (100 mL, $H_2O$: ethanol 1:9), filtering through paper, and adding additional ethanol (10–20 mL) to yield the desired 6,6-difluoro-1,12-diamino-4,9-diaza-dodecane as the tetrahydrobromide salt: white crystals 1.2 g, (49%).

Calc'd for $C_{10}H_{28}Br_4F_2N_4$: C, 21.37; H, 5.02; N, 9.97. Found: C, 20.97; H, 4.75; N, 10.01.

PREPARATION OF 2,2,11,11-TETRAFLUORO-4,12-DIAMINO-4,9-DIAZA-OCTANE

1-Phthalimido-2,2-difluoro-3-butene

To a stirred mixture of 2,2-difluoro-1,4-butanediol (12.97 g, 103 mM), dry pyridine (65 mL) and dichloromethane (200 mL) is slowly added a solution of methanesulfonylchloride (23.6 g) in dichloromethane (50 mL). Stirring is continued overnight. The reaction mixture is washed with 2N HCl (twice), followed by 10% aqueous $NaHCO_3$ until neutral, and then with water. The organic layer is dried ($MgSO_4$) and upon evaporation of the solvents, a slightly yellow oil is obtained. Crystallization is induced by scratching the oil with dry ether, to yield the compound 1,4-bis-methanesulfonyloxy-2,2-difluorobutane as white crystals: 22.3 g (77%).

The compound 1,4-bis-methanesulfonyloxy-2,2-difluorobutane (20 g, 71 mM) and diazabicycloundec-ene (21.6 g, 142 mM) are stirred with dry tetrahydrofuran (150 mL) and heated overnight at 80° C. under nitrogen. The solvents are removed under vacuum, and the residual oil is dissolved in dichloromethane, washed with 1N HCl (twice), brine (twice) and dried ($Na_2SO_4$). Evaporation of the solvents yields the compound 1-methanesulfonyl-2,2-difluoro-3-butene as an oil: 11.2 g (85%).

The compound 1-methanesulfonyl-2,2-difluoro-3-butene (11.2 g, 60.2 mM), potassium phthalide (12.3 g, 66.4 mM) and dry dimethylformamide (30 mL) are stirred and heated (bath temperature 110° C.) under nitrogen for 120 hours. After cooling to room temperature, the crude reaction product is precipitated by the addition of water (approximately 300 mL), filtered and dissolved in dichloromethane. The dichloromethane solution is washed with 1N potassium hydroxide (twice), water (twice), dried ($Na_2SO_4$) and evaporated to yield 1-phthalimido-2,2-difluoro-3-butene as beige-colored crystals: 11.9 g (83%).

1-p-Toluenesulfonamino-2,2-difluoro-3-butene

The compound 1-phthalimido-2,2-difluoro-3-butene (11.4 g, 48.1 mM) is heated for 20 hours. After cooling in an ice bath, the phthalic acid is removed via filtration and the filtrate evaporated. The residue so obtained is dissolved in water, extracted with ether (twice), evaporated to dryness and stripped with isopropanol. Trituration with ether yields hygroscopic crystals of 1-amino-2,2-difluoro-3-butene as the hydrochloride salt: 6.12 g, (88%).

To a stirred mixture of 1-amino-2,2-difluoro-3-butene hydrochloride (6.1 g, 42.5 mM), 50 mL of dry dichloromethane and triethylamine (8.74 g, 2 equivalents), all of which have been cooled in an ice bath, is slowly added a solution of tosyl chloride (8.1 g, 1 equivalent) in 50 mL of dichloromethane. Stirring is continued overnight at room temperature, additional dichloromethane is added to the reaction mixture, and the resulting organic layer is washed with 1N HCl (twice), water (twice) and dried ($Na_2SO_4$). Evaporation of the solvent yields a brown semi-solid material (9.66 g), which is purified via flash chromatography on silica (300 g, eluent: ethyl acetate/petroleum ether 20–80; fraction size 100 mL). Fractions 17–25 are combined and evaporated to yield 1-p-toluenesulfonamino-2,2-difluoro-3-butene as white crystals; 4.8 g (43%). The desired compound can be recrystallized from ether/petroleum ether to yield very fine, cotton-like, needles.

Anal. Calc'd for $C_{11}H_{13}F_2NO_2S$: C, 50.56; H, 5.02; N, 5.36. Found: C, 50.93; H, 5.02; N, 5.45.

Following essentially the same procedure for the preparation of the 2,2-difluoro-4,12-diamino-4,9-diazadodecane, two equivalents of the 1-p-toluenesulfonamino-2,2-difluoro-3-butene, prepared above, is alkylated with one equivalent of 1,4-dibromobutane; the double bonds are oxidized to the corresponding dicarboxylic acid with $KMnO_4$ in aqueous acetic acid; the resulting dicarboxylic acids are reduced to the corresponding primary diols with borane-methylsulfide complex; the diols are mesylated with methanesulfonyl chloride; the mesyl derivative is reacted with potassium phthalimide to obtain the corresponding 1,12-diphthalimido derivative; and the phthaloyl and tosyl protecting groups are removed to obtain the desired 2,2,11,11-tetrafluoro-1,12-diamino-4,9-diaza-dodecane.

DEMONSTRATION OF THE ANTIPROLIFERATIVE EFFECT OF 6,6-DIFLUORO-1,12-DIAMINO-4,9-DIAZA-DODECANE

Morris rat hepatoma 7288C (HTC) cells are routinely grown as a suspension culture in Swim's 77 medium supplemented with 10% (V/V) dialysed horse serum, 11.0 mM glucose, 2 mM glutamine, 0.057 mM cystine, 5.9 mM NaHCO$_3$ and 50 mM of N-tris(hydroxymethyl)-methylglycine. The HTC cell cultures are incubated in the presence or absence of 1 m or 10 m of the compound 6,6-difluoro-1,12-diamino-4,9-diaza-dodecane and observed for a period of 11 days.

The cell culture medium is changed at day 2, to maintain cells in a logarithmic phase of growth. The actual cell numbers are determined by cell-counting and the relative cell growth is calculated taking into account the various dilution factors employed. The percent inhibition of cell growth is calculated according to the equation:

$$100 - 100 \left[ \frac{N_t n - N_t O}{N_c n - N_c O} \right]$$

wherein $N_c O$ is the relative growth of control cultures at time=O, $N_c n$ is the relative growth of control cultures at time=n, $N_t O$ is the relative growth of test cultures at time=O, and $N_t n$ is the relative growth of test cultures at time=n.

Table I illustrates that administration of 1 μm of 6,6-difluoro-1,12-diamino-4,9-diaza-dodecane to the culture medium inhibits cell growth by 54% at the end of 4 days, whereas the administration of 10 μm of the drug inhibits cell growth by 77% at the end of the same period of time.

TABLE I

Effects of 6,6-Difluoro-1,12-Diamino-4,9-Diaza-Dodecane On HTC Cell Growth

| Time (days) | Relative Growth | | | (%) Inhibition of Cell Growth | |
|---|---|---|---|---|---|
| | Control | 1 μm of Cmpd | 10 μm of Cmpd | 1 μm of Cmpd | 10 μm of Cmpd |
| 0 | 1.00 | 1.00 | 1.00 | 0 | 0 |
| 1 | 1.89 | 1.36 | 1.24 | 60 | 73 |
| 2 | 3.63 | 2.50 | 1.94 | 43 | 64 |
| 3 | 6.66 | 5.24 | 3.56 | 25 | 55 |
| 4 | 14.11 | 6.98 | 4.07 | 54 | 77 |

We claim:

1. A gem-dihalo or tetrahalo-1,12-diamino-4,9-diaza-dodecane derivative having the formula

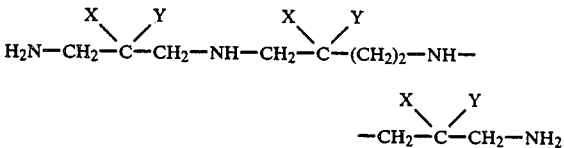

wherein X and Y represent hydrogen or halogen, with the proviso that in the case of the dihalo derivatives both halogens are present on one and only one carbon atom, and in the case of the tetrahalo derivatives the compounds are 2,2,11,11-halo-substituted; and the pharmaceutically acceptable salts thereof.

2. A compound according to claim 1 wherein the halogens are at the 6,6-position and the pharmaceutically acceptable salts thereof.

3. A tetrahalo-1,12-diamino-4,9-diazo-dodecane derivative of the formula

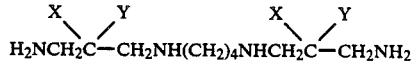

and the pharmaceutically acceptable salts thereof wherein X and Y are halogeno.

4. 6,6-Difluoro-1,12-diamino-4,9-diaza-dodecane and its pharmaceutically acceptable salts.

5. 2,2-difluoro-1,12-diamino-4,9-diazo-dodecane and its pharmaceutically acceptable salts.

* * * * *